(12) United States Patent
Chamberlain et al.

(10) Patent No.: US 7,132,518 B2
(45) Date of Patent: Nov. 7, 2006

(54) MONO- AND BIS-HYDRAZONE PIGMENTS

(75) Inventors: Terence Chamberlain, Cincinnati, OH (US); Norman W. Smith, Cincinnati, OH (US); Donald T. DeRussy, Mason, OH (US)

(73) Assignee: Sun Chemical Corporation, Parsippany, NJ (US)

( * ) Notice: Subject to any disclaimer, the term of this patent is extended or adjusted under 35 U.S.C. 154(b) by 0 days.

(21) Appl. No.: 11/209,216

(22) Filed: Aug. 23, 2005

(65) Prior Publication Data

US 2005/0288496 A1    Dec. 29, 2005

Related U.S. Application Data

(62) Division of application No. 10/240,990, filed as application No. PCT/US01/10863 on Apr. 3, 2001, now Pat. No. 6,965,019.

(60) Provisional application No. 60/194,236, filed on Apr. 3, 2000.

(51) Int. Cl.
*C09B 56/18* (2006.01)
(52) U.S. Cl. .................. 534/758; 548/519; 106/496
(58) Field of Classification Search ................ 534/758; 548/519
See application file for complete search history.

(56) References Cited

U.S. PATENT DOCUMENTS 4,460,768 A    7/1984   Iqbal et al. ................ 548/105
4,508,899 A    4/1985   Chamberlain ............... 544/225

FOREIGN PATENT DOCUMENTS

| BE | 509646 A | 2/1954 |
| GB | 1 435 704 | 5/1976 |
| GB | 1 544 560 | 4/1979 |
| WO | WO 01/74950 A2 | 10/2001 |

OTHER PUBLICATIONS

El-Kousy et al., Chemical Abstracts, 123:198688, 1995.*
Li et al., Chemical Abstracts, 115:183008, 1991.*
Mumm; Muenchmeyer: "Phenyllydrazone of Phenyl-Kiketo-Pyrroline":; Chemische Berichte; 1910; vol. 43 p. 3358.
El-Kousy et al., "A Study on Rearrangement of Arylazo Furanones and Pyrrolinones":; Oct. 9, 1995, vol. 123, No. 15; p. 1236 col. 2, Chemical Abstracts.
L. Capuano; P. Morsdorf; "Chemie Der 2,3-Dihydro-2,3-Diiminofurane"; Jul. 30, 1982; Liebigs Annalen Der Chemie; vol. 12, pp. 2178-2188.
F. Lovren et al.; Reactivity and Microbiological Activity of 2-Methyl-3-Carboethoxy-5-Pyrrolinone Derivatives; 1992; vol. 47, pp. 773-776, Pharmazie.
G. Kollenz; Synthesis of Heterocyclical Compounds; 1971; Monatshefte Chemie; vol. 102, No. 1, pp. 108-113.

* cited by examiner

*Primary Examiner*—Fiona T. Powers

(57) ABSTRACT

Mono- and Bis-Azo/Hydrazone Pyrrole Pigments and Methods for preparing same.

6 Claims, 6 Drawing Sheets

Formula IV

MONO- AND BIS-HYDRAZONE PIGMENTS

This application is a divisional application of the patent application Ser. No. 10/240,990, filed Jan. 6, 2003, now U.S. Pat. No. 6,965,019.

BACKGROUND OF THE INVENTION

1. Field of the Invention

The present invention relates to hydrazone pigments and their preparation. More particularly, the present invention relates to mono-azo/hydrazone or bis-azo/hydrazone pigments derived from 2-aryl-3-alkoxycarbonyl-5-pyrrolinones and 2-aryl-5-pyrrolinones intermediates.

2. Description of the Prior Art

Lovren et al., 47 *Pharmazie* 773–776 (1992) discloses the synthesis of azo/hydrazones where 2-methyl-3-carboethoxy-5-pyrrolinones are reacted with aromatic aldehydes and aryldiazonium (azo) salts.

SUMMARY OF THE INVENTION

In one aspect, the present invention relates to a mono-azo/hydrazone pigment whose structure conforms to the formula (I):

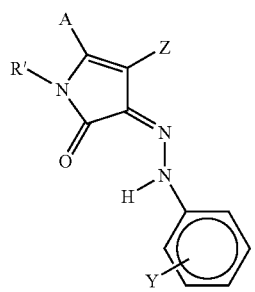

wherein: A is a substituted or unsubstituted aryl or substituted or unsubstituted heteroaryl radical; R' is hydrogen, alkyl, aralkyl, aryl or heteroaryl; Z is hydrogen, CO—X—B, CN, or COCH$_3$ where B is hydrogen, or a primary aliphatic, carbocyclic, aryl or heterocyclic radical; Y is hydrogen, alkyl, alkoxy, amine, nitro, carboxylic acid, carboxylic acid ester, or a substituted or unsubstituted fused ring; and X is a divalent O or NH radical.

In another aspect, the present invention relates to a bis-azo/hydrazone pigment whose structure conforms to the formula (II):

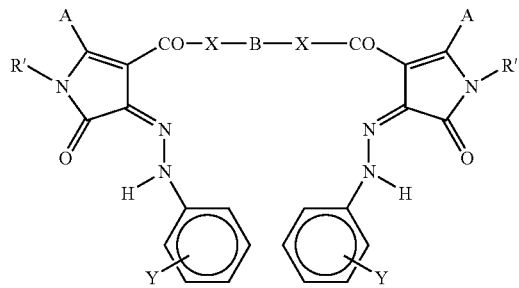

wherein:
A, R', Y and X are as previously defined; and B is a divalent aliphatic, carbocyclic or heterocyclic radical, a divalent aryl or heteroaryl radical.

In another aspect, the present invention relates to a bis-azo/hydrazone pigment whose structure conforms to the formula (III)

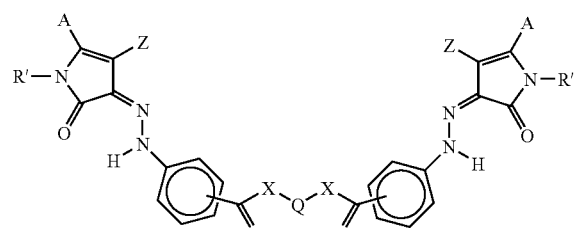

wherein: A, R', Z and X are as previously defined and Q is a divalent aliphatic, carbocyclic or heterocyclic radical, a substituted or unsubstituted aryl radical, a divalent substituted or unsubstituted biphenyl radical or a divalent substituted or unsubstituted heteroaryl radical, where the substituent may be halogen, alkyl or alkoxy.

In yet another aspect, the present invention relates to a bis-azo/hydrazone pigment whose structure conforms to the formula (IV)

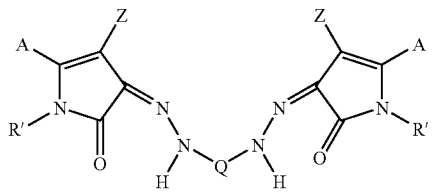

wherein: A, R', and Z are as previously defined; and Q is a divalent substituted or unsubstituted aryl radical, a divalent substituted biphenyl radical or a divalent substituted or unsubstituted heteroaryl radical, where the substituent may be halogen, alkyl or alkoxy.

Yet another embodiment of the present invention relates to a bis-azo/hydrazone pigment whose structure conforms to the formula (V)

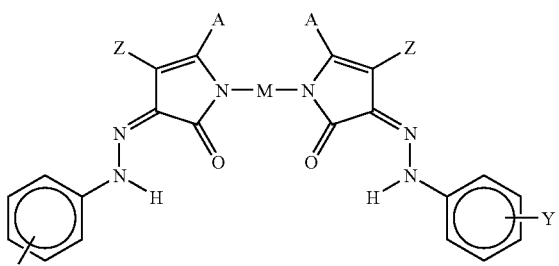

wherein: A, Y, and Z are as previously defined; and M is a divalent alkyl, substituted or unsubstituted aryl or substituted or unsubstituted heteroaryl radical, where the substituent may be halogen, alkyl or alkoxy.

The invention also relates to a process for preparing the mono-azo/hydrazone pigments of formula I, in which at least one aromatic hydrazine having the formula (VI):

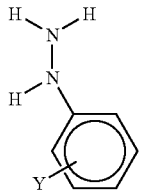

wherein: Y is as previously defined; is reacted with a compound of the formula:

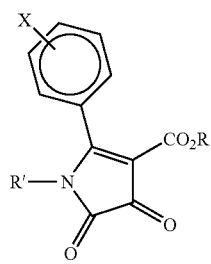

wherein: X and R' are as previously defined and R is hydrogen.

The invention also relates to an alternative process for preparing the mono-azo/hydrazone pigments of formula I, in which compound having the formula:

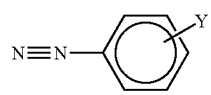

wherein: Y is as previously defined; is reacted with a compound of the following formula:

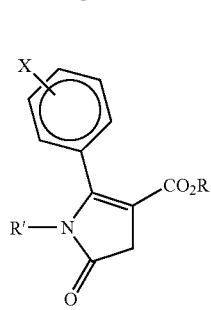

wherein: X and R are as previously defined and R' is hydrogen.

The invention also relates to a process for preparing higher molecular weight mono-azo/hydra zone pigments of formula I, in which at least one aromatic hydrazine having the formula:

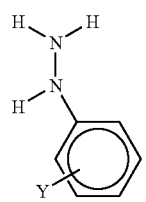

wherein: Y is as previously defined; is reacted with a compound of the following formula:

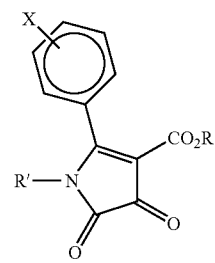

wherein: X and R are as previously defined; and R' is alkyl, aralkyl, aryl or heteroaryl.

The invention also relates to an alternative process for preparing the mono-azo/hydrazone pigments of formula I, in which a compound having the formula:

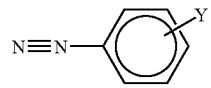

wherein: Y is as previously defined; is reacted with a compound of the following formula:

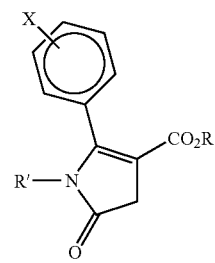

wherein: X and R are as previously defined; and R' is alkyl, aralkyl, aryl or heteroaryl.

In another aspect, the invention relates to a process for preparing the bis-azo/hydrazone pigments of formula II, in which diamines of the formula $H_2N-B-NH_2$ (where B is as previously defined; with the exception that B cannot be hydrogen) are reacted with a compound of the formula (VIII):

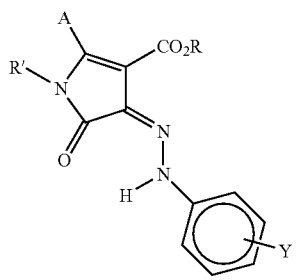

wherein: A, R' and Y are as previously defined; and R is a straight or branched chain $C_1$–$C_{18}$ alkyl, $C_7$–$C_{18}$ aralkyl or aryl.

The present invention also relates to an alternative process for preparing the bis-azo/hydrazone pigments of formula II, in which a diol of the formula HO—B—OH (where B is as previously defined above with the exception that B cannot be hydrogen) is reacted with a compound of the formula (VIII):

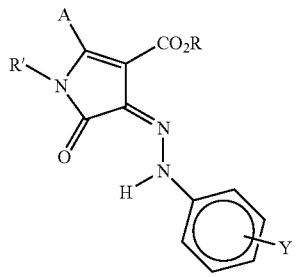

wherein: A, R' and Y are as previously defined; and R is a straight or branched chain $C_1$–$C_{18}$ alkyl, $C_7$–$C_{18}$ aralkyl or aryl.

The present invention also relates to a process for preparing the bis-azo/hydrazone pigments of the formula (III):

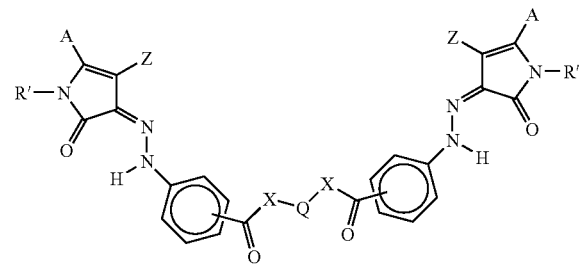

wherein: A, R', Z and X are as previously defined; and Q is a divalent aliphatic, carbocyclic or heterocyclic radical, a substituted or unsubstituted aryl radical, a divalent substituted or unsubstituted biphenyl radical or a divalent substituted or unsubstituted heteroaryl radical, where the substituent may be halogen, alkyl or alkoxy;

comprising reacting a diamine of the formula $H_2N$—Q—$NH_2$, where Q is a divalent aliphatic, carbocyclic or heterocyclic radical, a divalent aryl radical or a divalent heteroaryl radical, with a compound of the formula (IX):

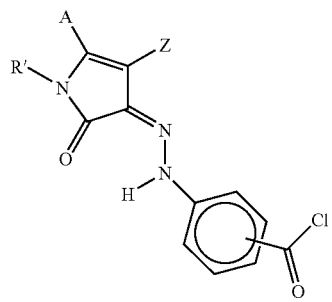

wherein: A, R' and Z are as previously defined.

The present invention also relates to an alternative process for preparing the bis-azo/hydrazone pigments of formula III comprising reacting a diol of the formula OH—Q—OH, where Q is as previously defined with a compound of the formula (IX):

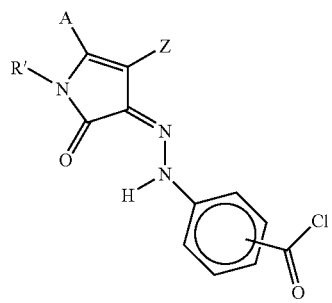

In another aspect, the present invention is a process for preparing the bis-azo/hydrazone pigments of the formula (IV):

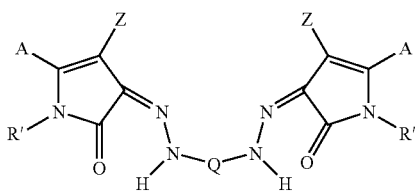

wherein: A, R' and Z are as previously defined and Q is a divalent substituted or unsubstituted aryl radical, a divalent substituted heteroaryl radical, where the substituent may be halogen, alkyl or alkoxy; comprising reacting a diamine of the formula $H_2NH$—Q—$HNH_2$ where Q is a divalent aliphatic, carbocyclic or heterocyclic radical, a divalent aryl radical or divalent heteroaryl radical, with a compound of the formula:

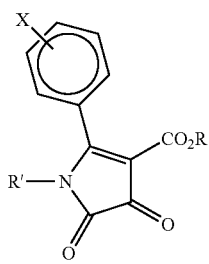

wherein: X, R' and R are as previously defined.

In another aspect, the present invention is an alternative process for preparing the bis-azo/hydrazone pigments of formula (IV) comprising reacting a compound of the formula $N_2$—Q—$N_2$ where Q is a divalent aliphatic, carbocyclic or heterocyclic radical, a divalent aryl radical or divalent heteroaryl radical, with a compound of the formula:

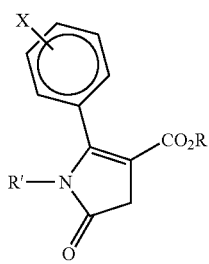

wherein: X, R' and R are as previously defined.

In another aspect, the present invention is a process for preparing the bis-azo/hydrazone pigments of the formula (V):

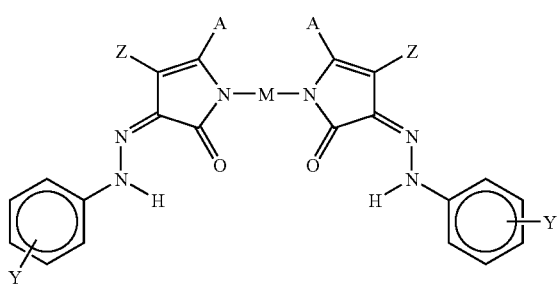

wherein: A, Z, Y, and M are as previously defined; comprising reacting a diamine of the formula $H_2N$—M—$NH_2$ where M is a divalent aliphatic, carbocyclic or heterocyclic radical, a divalent aryl radical or divalent heteroaryl radical, with a compound of the formula:

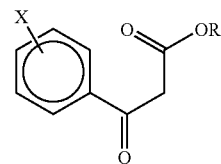

wherein: X and R are as previously defined; to form a compound of the formula:

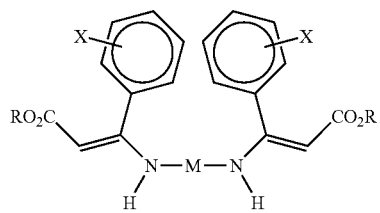

wherein: X, R and M are as previously defined; which is then reacted with oxalyl chloride $(COCl)_2$ to produce compound of the formula:

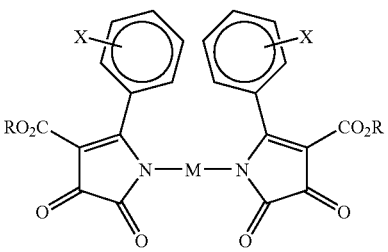

wherein: X, R and M are as previously defined; which is then reacted with a compound of the formula:

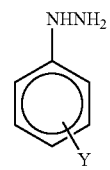

wherein: Y is as previously defined.

In another aspect, the present invention is an alternative process for preparing the bis-azo/hydrazone pigments of formula (V) comprising reacting a compound of the formula:

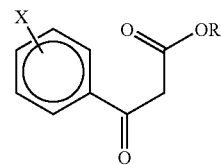

wherein: X and R are as, previously defined; with a compound of the formula $ClCH_2CO_2R$ wherein: R is as previously defined; to produce a compound of the formula:

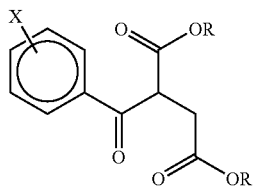

wherein: X and R are as previously defined; which is then reacted with a diamine of the formula $HN_2$—M—$HN_2$ where M is as previously defined; to form a compound of the formula:

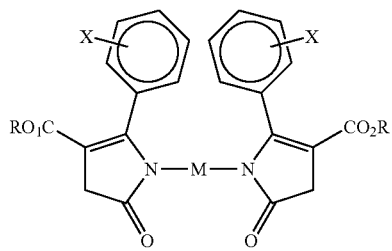

wherein: X, R and M are as previously defined; which is then reacted with a compound of the formula:

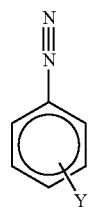

wherein: Y is as previously defined.

BRIEF DESCRIPTION OF THE DRAWINGS

Those of ordinary skill in the art will recognize that the structures shown in the Figures depicting the azo/hydrazone colorants of the present invention are also meant to include the corresponding tautomeric compounds and the possible configurational isomers of each tautomeric form. Thus, the hydrazone compounds of the present invention include their corresponding azo forms.

Therefore, these compounds will be referred to as azo/hydrazones in recognition of their tautomeric nature.

In the First route (lower portion of FIG. 6) an aryloylsuccinate diester is reacted with a diamine to form a bis-ketopyrrole coupler which is then reacted with a diazonium compound.

In the second route (upper portion of FIG. 6) a diamine is reacted with a alkylaryloylacetate to produce an intermediate bis(aminocinnamic acid ester) which is then reacted with an oxalylchloride to form a bis-diketopyrrole which is subsequently reacted with arylhydrazine to produce the desired bis-azo/hydrazone.

DETAILED DESCRIPTION OF THE PREFERRED EMBODIMENTS

As summarized above, the present invention relates to a mono-azo/hydrazone pyrrole whose structure conforms to the following formula (I):

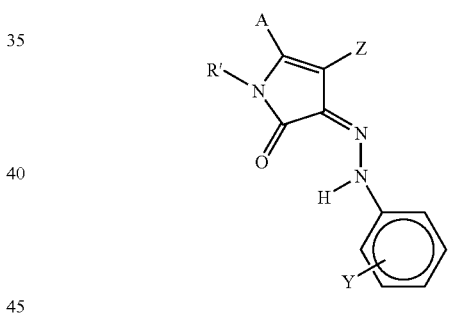

wherein: A, R', Y and Z are as previously defined.

Those of ordinary skill in the art will recognize that the aryl ring of formula I can have multiple Y substituents other than hydrogen, which may be the same or different. Preferred embodiments include compounds in which A is a substituted or unsubstituted aryl radical; compounds in which Y is a nitro group, and compounds in which Z is CO—X—B, where X and B are as previously defined.

Dual Synthetic Routes to Mono-Azo/Hydrazone Pyrroles

Figure 1:
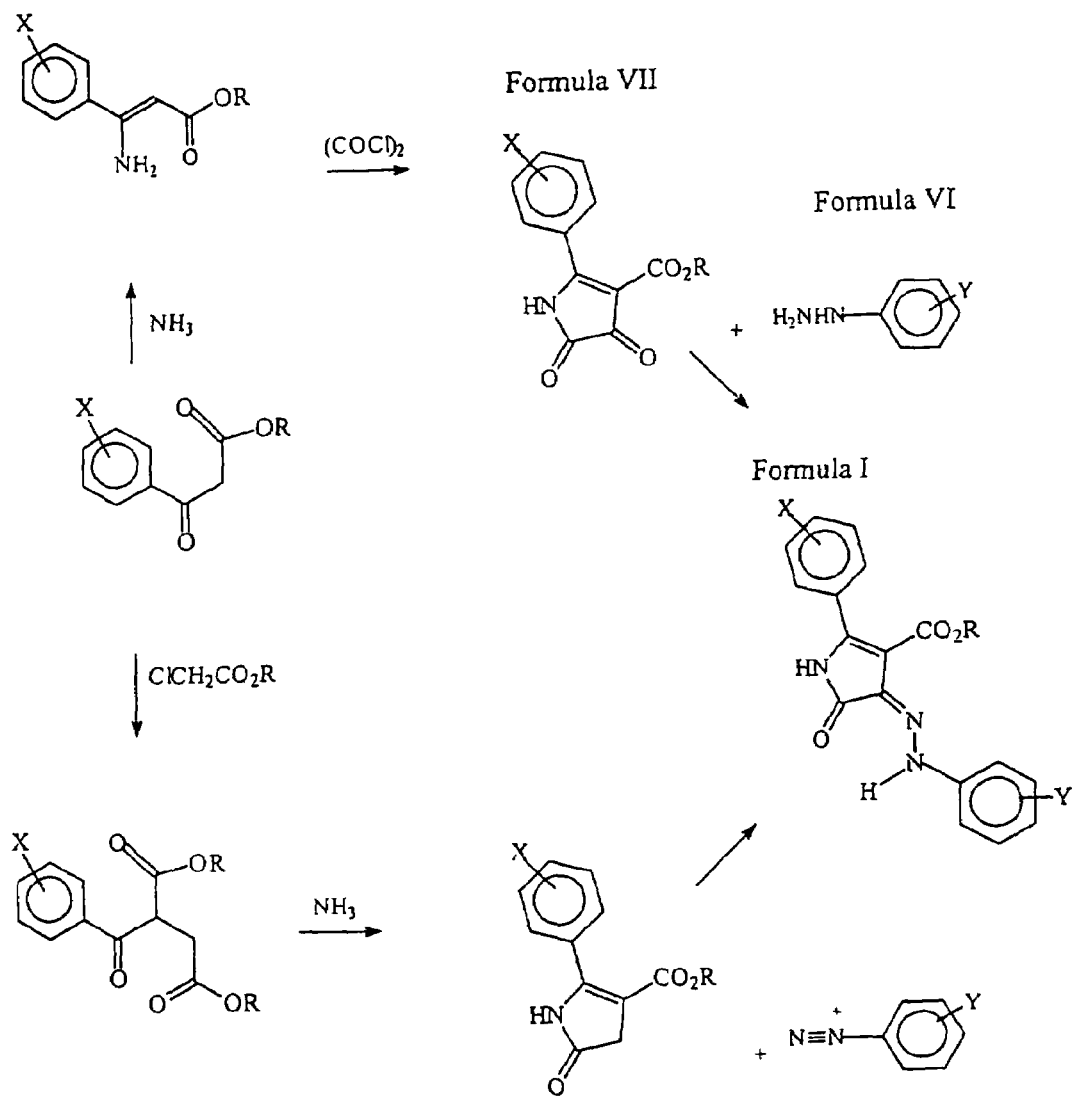
FIG. 1 illustrates two independent synthetic routes for producing a mono-azo/hydrazone of the present invention beginning with the same starting material.

The mono-azo/hydrazones of the present invention can be synthesized from readily available starting materials using conventional synthetic organic reactions. FIG. 1 illustrates two synthesis routes for production of a mono-azo/hydrazone of the present invention where A is a substituted or unsubstituted aryl radical. Both syntheses begin with the same substituted or unsubstituted alkylaryloylacetate as the starting material.

The lower portion of FIG. 1 illustrates an alkylation reaction between the alkylaryloylacetate and an alkylchloroacetate to produce an aryloylsuccinate diester and hydrogen chloride (not shown). The reaction is normally run in the presence of a base, typically sodium carbonate, which acts to scavenge the hydrogen chloride by-product.

The aryloylsuccinate diester may optionally be separated from the reaction mixture before being subsequently reacted with either ammonia or, preferably, ammonium salts, in an amination/cyclization reaction to produce a ketopyrrole, which is isolated, typically by filtration. An excess of ketopyrrole (3–5 molar percent) is subsequently reacted with a substituted or unsubstituted aryldiazonium salt in a conventional coupling reaction to produce a mono-azo/hydrazone pyrrole of the present invention.

An alternative synthesis route is shown in the upper portion of FIG. 1. The synthesis also begins with alkylaryloylacetate as the starting material, which is reacted with ammonia in an amination reaction to produce water and the corresponding aminocinnamic acid ester derivative, which is then isolated, preferably by distillation.

The isolated aminocinnamic acid ester derivative is subsequently reacted with oxalyl chloride to produce the corresponding di-ketopyrrole and hydrogen chloride by-product. The di-ketopyrrole is isolated by filtration and subsequently condensed with an arylhydrazine to produce the desired mono-azo/hydrazone pyrrole of the present invention and water. The mono-azo/hydrazone pyrrole may be conveniently isolated by filtration.

The alkylaryloylacetate starting material in FIG. 1 is either commercially available or may easily be prepared by reacting a dialkylcarbonate with an appropriate arylmethyl ketone under basic conditions which are well known to those of ordinary skill in the art.

While the same mono-azo/hydrazone compound can be generated by two separate synthesis routes with different intermediates, each synthesis has its own advantages such as yield, quality and compatibility for in-situ preparation. The advantages of each synthetic route will be readily apparent to those of ordinary skill in the art.

Figure 2:
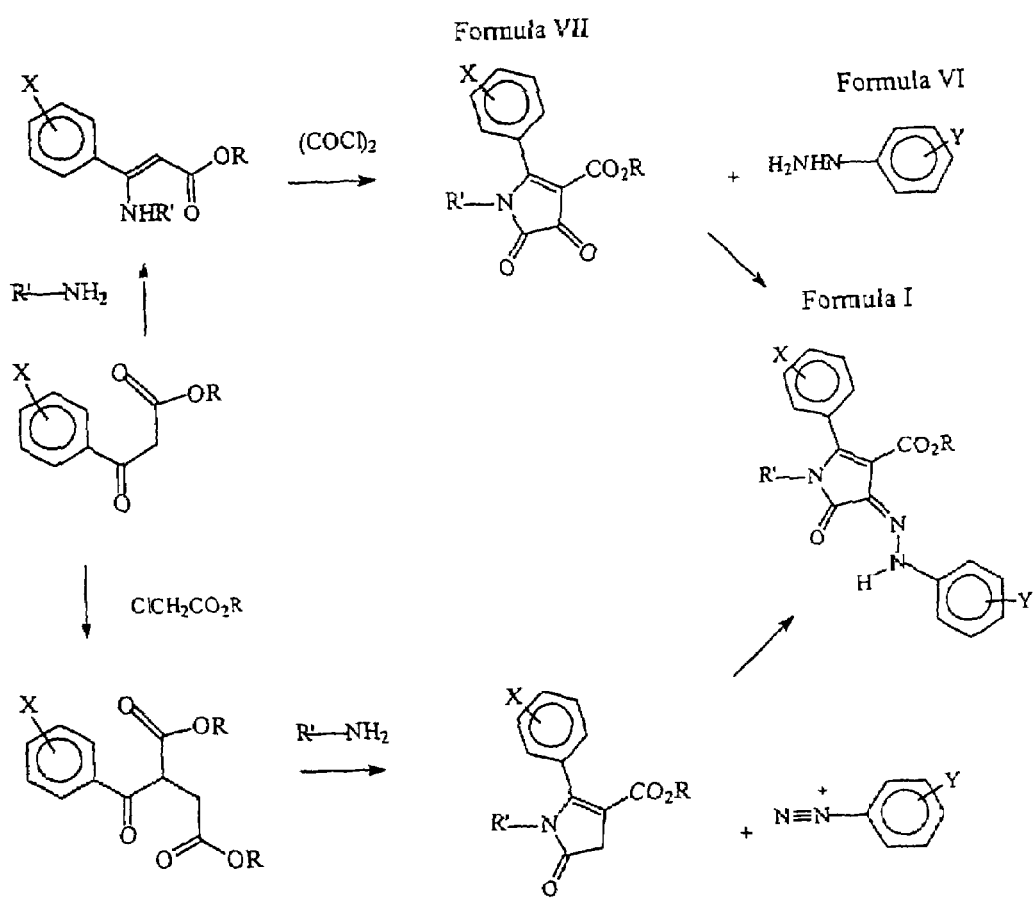
FIG. 2 shows two independent synthetic routes for producing a derivatized mono-azo/hydrazone of the present invention beginning with the same starting material.

Those of ordinary skill in the art will readily understand that the synthesis routes in FIG. 1 can be easily expanded by, for example, replacing the ammonia used as a reactant in either synthetic route with an amine NH2—R' (where R' may be an alkyl radical, an aralkyl radical, an aryl radical, or heteroaryl radical) to produce a derivatized mono-azo/hydrazone pyrrole, as shown in FIG. 2. One important consequence of derivatizing the mono-azo/hydrazone compound is that proper selection of the R' functional group permits those of ordinary skill in the art to "tailor" the compound to adjust its solubility to produce either a pigment (insoluble) or a dyestuff (soluble) depending on the particular system of interest.

Reactions Based on the Ester Functional Group

Figure 3:
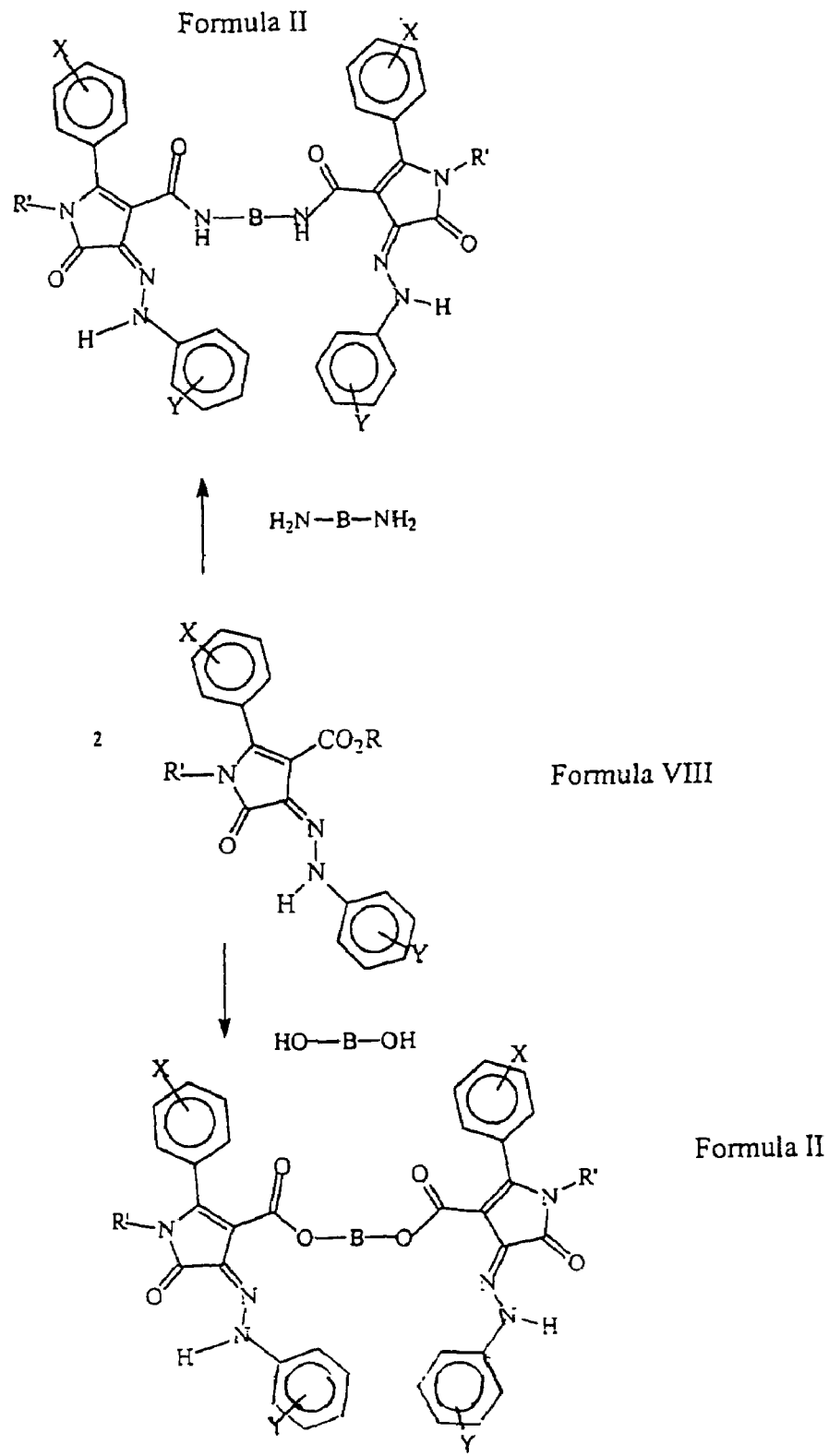
FIG. 3 depicts reacting a mono-azo/hydrazone of the present invention with either a diamine or a diol to produce a higher molecular weight bis-amide or bis-ester, respectively.

The mono-azo/hydrazone pyrrole of the present invention may have an ester group (Z is CO—X—B, with X being a divalent oxygen radical in formula I above). As shown in FIG. 3, this embodiment of the invention may be condensed with a suitable diamine to form a higher molecular weight bis-amide, or reacted with an appropriate diol to form the corresponding bis-ester, and an alkanol byproduct R—OH (not shown). Preferably, two moles of mono-azo/hydrazone are used to produce the corresponding bis-ester or bis-amide, respectively, together with an alkanol (R—OH) by-product (not shown). More preferably, a 5 to 10 molar percent excess of diol or diamine is employed.

Such condensations are conventional reactions and well known to those of ordinary skill in the art and typically are run at a reaction temperature of 150 to 200° C. in a high boiling organic solvent such as dichlorobenzene or trichlorobenzene. Preferably, a 5 to 10 molar percent excess of diol or diamine is employed. The resulting bis-ester and bis-amide products are solids and may be conveniently isolated by filtration.

The bis-azo/hydrazone pyrroles of the present invention thus include compounds whose structure conforms to the formula (II)

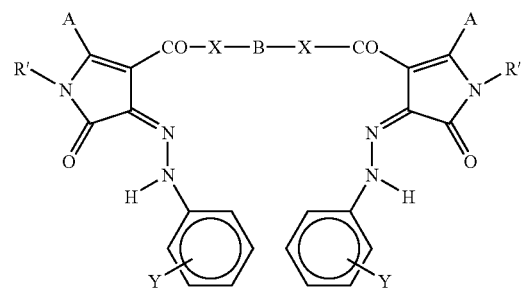

wherein: A, R', Y, X and B are as previously defined. Preferred embodiments include those compounds where A is a substituted or unsubstituted aryl radical; and compounds where Y is a nitro group.

Those of ordinary skill in the art will readily recognize that the difunctional reactants (diols and diamines) illustrated in FIG. 3 can be replaced with monofunctional reactants to produce the corresponding monoesters and monoamides, respectively. Similarly, the reactants can be triols or triamines.

Reactions Based on Aromatic Ring Substituents

The present invention includes other bis-azo/hydrazone compounds in addition to the compounds of formula II. Thus, FIG. 4 illustrates another way to further react the mono-azo/hydrazone pyrroles of the present invention to produce higher molecular weight colorants.

This synthesis route is based on the reactivity of substituents located on the aromatic ring (i.e., where Y of formula II is a carboxylic acid, hydroxy or amine). Thus, as shown in FIG. 4, the carboxylic acid group can be converted to an acid chloride which in turn is reacted with a diamine or a diol to produce a bis-amide or bis-ester in analogous fashion to the synthesis shown in FIG. 3.

Figure 4:
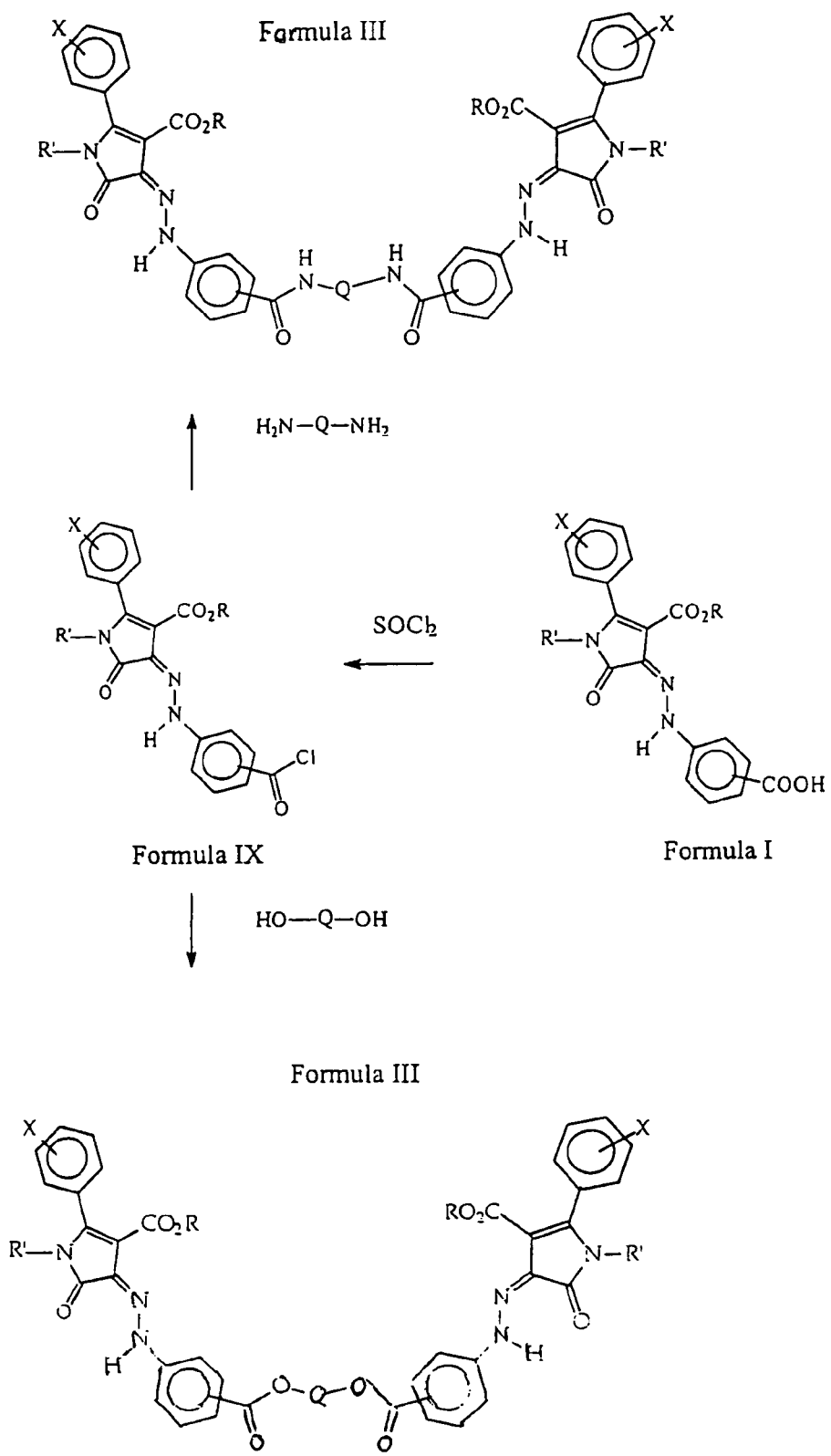
FIG. 4 illustrates an alternative synthesis suitable for substantially increasing the molecular weight of the mono-azo/hydrazone pyrrole of the present invention.

More particularly, FIG. 4 illustrates a specific embodiment of a mono-azo/hydrazone where A is a substituted or unsubstituted aryl group and Y is a carboxylic acid, and its conversion to the corresponding, higher molecular weight bis-azo/hydrazone. The carboxylic acid group of the mono-azo/hydrazone may then be converted to an acid chloride (using for example, thionyl chloride, oxalyl chloride, phosphoryl chloride, etc.) to produce the corresponding mono-azo/hydrazone acid chloride (and by-products such as $SO_2$ and HCl).

The acid chloride may be optionally isolated prior to reaction with either a diamine or diol to produce the corresponding bis-amide or bis-ester, respectively, which may be isolated from the by-products by filtration. A 5–10% molar excess of the diamine or diol is preferably employed. High boiling aromatic solvents such as dichlorobenzene and trichlorobenzene are typically used in these reactions, which are run at from 100 to 200° C.

The bis-azo/hydrazone pyrroles of the present invention include compounds whose structure conforms to the formula (III):

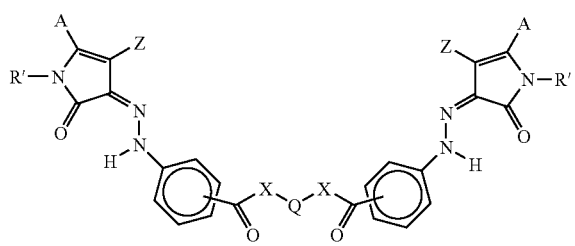

wherein: A, R', X and Q are as previously defined. Preferred compounds include those in which A is a substituted or unsubstituted aryl radical.

Those of ordinary skill in the art will readily recognize that the difunctional reactants (diols and diamines) employed in the synthesis illustrated in FIG. 4 can be replaced with monofunctional reactants to produce the corresponding monoesters and monoamides, respectively. Similarly, the reactants can be triols or triamines.

Synthesis of Bis-azo/hydrazones Using Aryltetrazonium Salts

Figure 5:
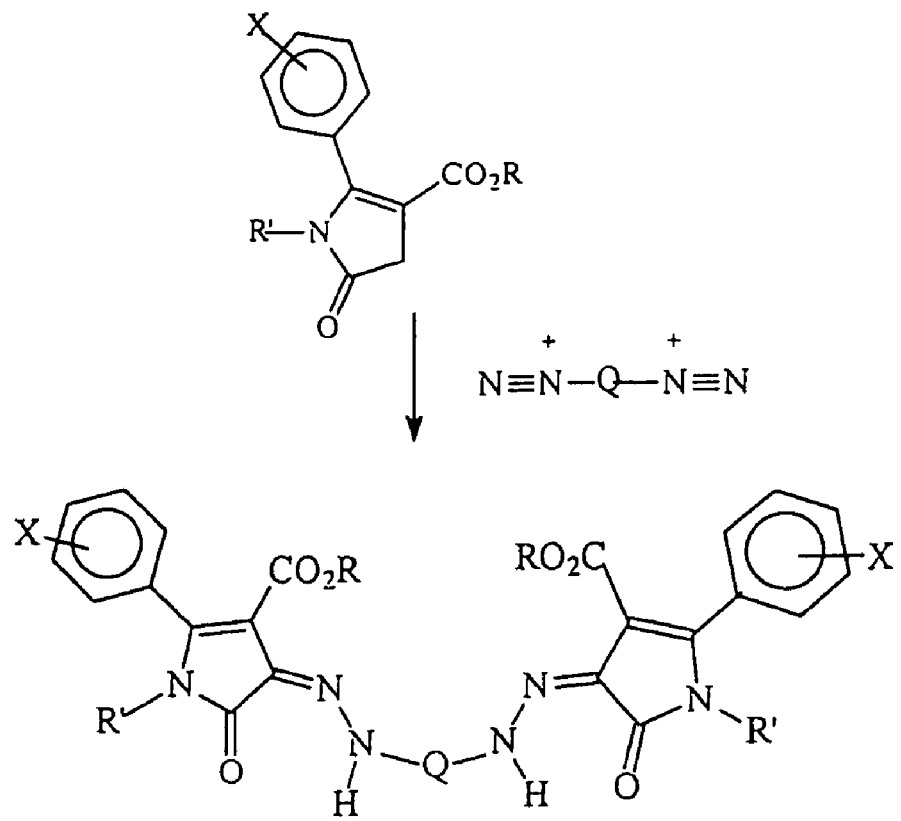
FIG. 5 shows two independent synthetic routes for making a bis-azo/hydrazone of the present invention where in the first route a ketopyrrole coupler is reacted with a tetrazonium salt, and in the second route a di-ketopyrrole is reacted with a bis-arylhydrazine.
Figure 5:
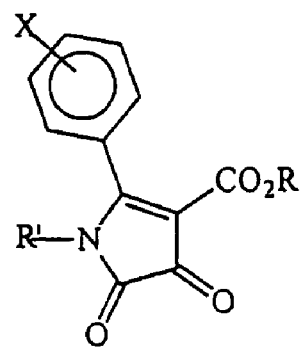

The upper portion of FIG. 5 shows the synthesis of a bis-azo/hydrazone pyrrole in which a ketopyrrole coupler is reacted with an aryltetraazonium salt, produced from a corresponding aryldiamine by reaction with sodium nitrite in an aqueous acid by tetrazotization.

The ketopyrrole coupler may be dissolved in methanol, ethanol, acetic acid or any suitable water-miscible solvent then reacted with the aqueous aryltetraazonium salt at a temperature ranging from 0° C. to room temperature at a pH ranging from 1 to 7 to produce the desired bis-azo/hydrazone pyrrole product of the formula (IV):

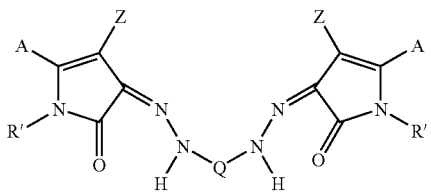

wherein: A, R', Z and Q are as previously defined.

By substituting the aryl diazonium salt shown in FIG. 1 with a aryltetraazonium salt, one can produce yet another class of bis-azo/hydrazone pyrroles represented by formula IV.

Preferred embodiments include those compounds where A is a substituted or unsubstituted aryl radical; where Q is biphenyl substituted with halogen, alkyl or alkoxy; and where Z is CO—X—B (where X and B are as previously defined.

The lower portion of FIG. 5 shows an alternative synthesis of the bis-azo/hydrazone of formula IV in which a di-ketopyrrole is condensed with a bis-arylhydrazine. An acid catalyst, such as toluene sulfonic acid, may optionally be employed. The condensation reaction is run in suitable organic solvents at a temperature ranging from room temperature to 150° C. and more preferably at a temperature ranging from room temperature to 100° C.

Synthesis of Bis-azo/hydrazones Using A Diamine

Figure 6:
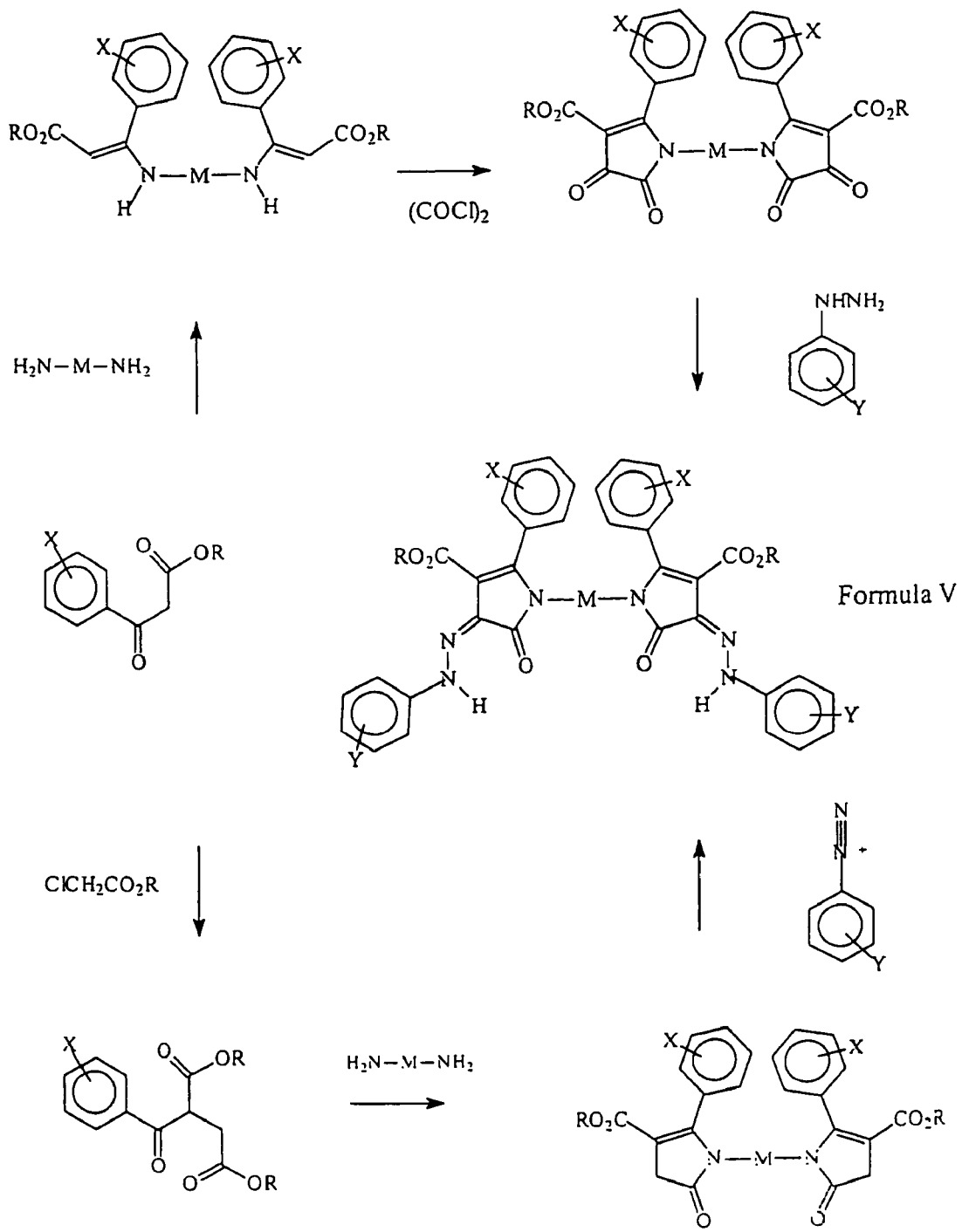
FIG. 6 depicts two independent synthetic routes for forming a bis-azo/hydrazone of the present invention.

FIG. 6 (lower portion) illustrates an alkylaryloylacetate, which is reacted in organic solvent with an alkylchloroacetate to produce the corresponding aryloylsuccinate diester, which is then preferably isolated by filtration.

The diester compound is subsequently reacted with an appropriate diamine to produce the corresponding bis-keto-pyrrole, which is isolated by filtration. The bis-ketopyrrole is then coupled with an aryldiazonium salt in water or a water-miscible solvent to produce a bis-azo/hydrazone pyrrole of formula V which may be isolated by filtration. The reaction conditions (solvent and temperature) are essentially the same as those discussed above for the corresponding synthesis shown in FIG. 2.

The upper portion of FIG. 6 illustrates an alternative synthesis route to produce the high-molecular weight bis-azo/hydrazone of formula V. More particularly, a alkylaryloylacetate starting material (shown in FIGS. 1 and 2) is reacted with an appropriate diamine in an organic solvent such as ethanol to produce a bis(aminocinnamic acid ester derivative) which is then isolated by filtration and reacted with oxalylchloride to produce a bis-diketopyrrole, which is isolated, preferably by filtration. The bis-diketopyrrole is then reacted with an arylhydrazine in an organic solvent to produce the bis-azo/hydrazone of the formula (V):

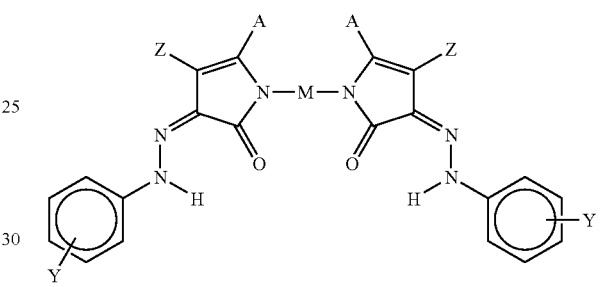

wherein: A, Z, M and Y are as previously defined.

The mono-azo/hydrazone pyrrole and derivatized mono-azo/hydrazone compounds illustrated in FIGS. 1 to 6 have utility as colorants or pigments per se. As discussed above, these compounds possess functional groups which can be further reacted to form the corresponding bis-azo/hydrazone pyrroles, which also have utility as higher molecular weight, generally less soluble, colorants.

The Examples below illustrate specific embodiments of the invention disclosed herein, and are not intended to limit the scope of the invention in any manner whatsoever.

EXAMPLE 1

2-Phenyl-3-ethoxycarbonyl-4-(2-nitrophenylhydrazonyl)-1H-5-pyrrolinone

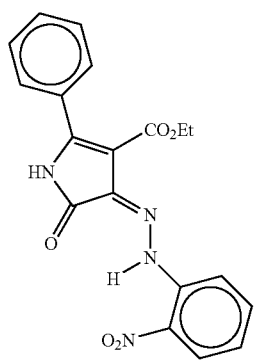

2-phenyl-3-ethoxycarbonyl-5-1H-pyrrole-4,5-dione (10.00 g, 0.0408 mol, 1.0 eq) and 97% o-nitrophenylhydrazine (moist solid containing 10% water) (7.16 g, 6.25 g pure, 0.0408 mol, 1.0 eq) were dissolved in glacial acetic acid (100 ml). The mixture was stirred at room temperature for 20 hours. The 2-phenyl-3-ethoxycarbonyl-4-(2-nitrophenyl-hydrazonyl)-1H-5-pyrrolinone product (14.17 g) was then isolated by filtration, washed with methanol, dried under vacuum at 60° C. and isolated as a bright orange solid in 91% yield. MP 244–246° C. (dec).

EXAMPLE 2

2-Phenyl-3-ethoxycarbonyl-4-(2,4-dinitrophenylhydrazonyl)-1H-5-pyrrolinone

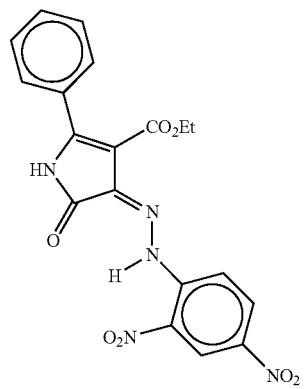

2-phenyl-3-ethoxycarbonyl-1H-pyrrole-4,5-dione (5.00 g, 0.0204 mol. 1.0 eq) and 2,4-dinitrophenylhydrazine (97% moist solid containing 30% water, 5.96 g, 4.04 g pure, 0.0204 mol, 1.0 eq) were dissolved in glacial acetic acid (50 ml). The mixture was stirred at room temperature for 2 hours, heated at reflux for an additional 2.5 hours, then cooled. The 2-phenyl-3-ethoxycarbonyl-4-(2,4-dinitro-phenylhydrazonyl)-1H-5-pyrrolinone product (5.63 g) was isolated by filtration, washed with methanol, dried under vacuum at 60° C. and isolated as a bright red solid in 65% yield. MP 304–306° C. (dec).

EXAMPLE 3

Alternative Synthesis

2-Phenyl-3-ethoxycarbonyl-4-(2,4-dinitrophenylhydrazonyl)-1H-5-pyrrolinone 2,4-dinitrophenylhydrazine (97% moist solid containing 30% water, 37.34 g, 25.36 g pure, 0.128 mol, 1.05 eq) was dissolved in ethanol (300 ml). The mixture was heated to 70° C. and concentrated sulfuric acid (4 drops) was added followed by 2-phenyl-3-ethoxycarbonyl-1H-pyrrole-4,5-dione (30.00 g. 0.122 mol, 1.0 eq) over 10 minutes. The mixture was stirred at reflux for 30 minutes and cooled. The 2-phenyl-3-ethoxycarbonyl-4-(2,4-dinitrophenylhydrazonyl)-1H-5-pyrrolinone product (43.6 g) was isolated by filtration, washed with methanol, dried under vacuum at 60° C. and isolated as a bright red solid in 84% yield. MP 304–306° C. (dec).

EXAMPLE 4

2-Phenyl-3-ethoxycarbonyl-4-(2-nitro-4-dichloro-phenylhydrazonyl)-1H-5-pyrrolinone

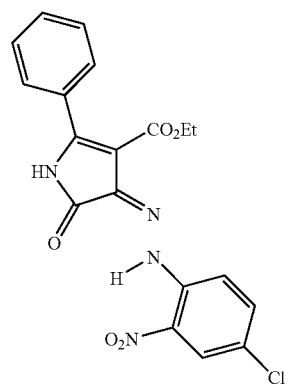

4-chloro-2-nitrophenylhydrazine hydrochloride (6.16 g, 0.0275 mol, 1.10 eq.) was partially dissolved in ethanol (75 ml). The mixture was heated to 70° C. and concentrated sulfuric acid (4 drops) was added, followed by 2-phenyl-3-ethoxycarbonyl-1H-pyrrole-4,5-dione (6.13 g, 0.025 mol, 1.0 eq.) over 10 minutes. The mixture was stirred at reflux for 1.5 hours and cooled. The 2-phenyl-3-ethoxycarbonyl-4-(2-nitro-4-chloro-phenylhydrazonyl)-1H-5-pyrrolinone product (7.65 g) was isolated by filtration, washed with methanol, dried under vacuum at 60° C. and isolated as a bright orange solid in 74% yield. MP 292–294° C. (dec).

EXAMPLE 5

Acrylic Paint Formulation

Thermosetting, organic solvent based, acrylic paint formulations were prepared from pigment samples of the present invention produced in Examples 1, 2 and 4 using conventional equipment and techniques. These paint formulations were each applied to a commercially available display tint card (Form 2C, the Leneta Company) and dried to produce a coating with a clean bright mastone. Corresponding tints were prepared by the addition of a standard amount of white pigment (titanium dioxide) to the original paint, which was then coated upon a second display card of the same type and dried. The tint cards were each exposed to simulated solar radiation (765 W/m$^2$ covering a wavelength band of 300–800 nm in a Suntest CPS Fadometer) along with acrylic paint coating formulations pigmented with commercially available pigments of similar color. After time intervals of 300 and 1000 hours, the color properties of an exposed portion of each coating was measured by a color computer and compared to the color properties of an unexposed portion of the same coating. The difference between the two readings, expressed by the DE value, is shown in the Table 1. The smaller the DE value the better the lightfastness of the pigment in that paint.

Commercial Pigments (Table 1)

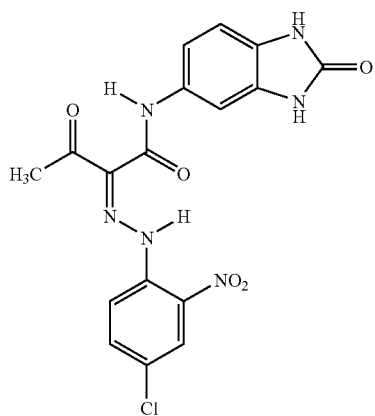

PO 36

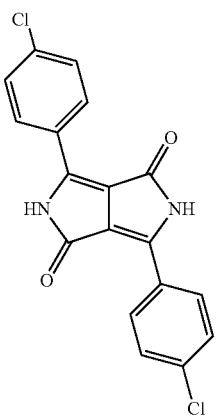

PR 254

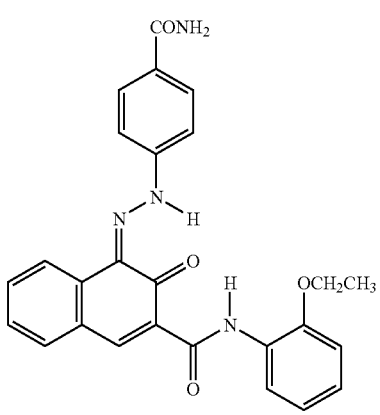

PR 170

EXAMPLES 1, 2 AND 4 (TABLE 1)

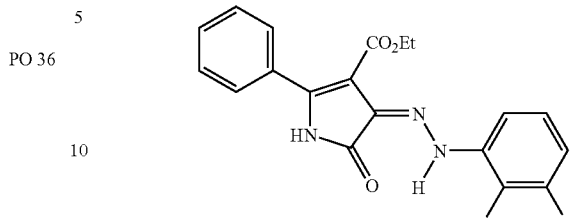

TABLE 1

| Sample | R1 | R2 | Hours | Masstone or tint | DE |
|---|---|---|---|---|---|
| 271-9136 PO 36 | | | 300 | Masstone | 1.14 |
| | | | 1000 | Masstone | 0.77 |
| | | | 300 | Tint | 0.64 |
| | | | 1000 | Tint | 2.98 |
| Example 1 (orange) | $NO_2$ | H | 300 | Masstone | 1.35 |
| | | | 1000 | Masstone | 3.23 |
| | | | 300 | Tint | 2.72 |
| | | | 1000 | Tint | 2.35 |
| Example 4 (orange) | $NO_2$ | Cl | 300 | Masstone | 0.75 |
| | | | 1500 | Masstone | 2.96 |
| | | | 300 | Tint | 0.44 |
| | | | 1500 | Tint | 5.15 |
| Ciba OPP Red BP PR 254 | | | 300 | Masstone | 1.16 |
| | | | 1000 | Masstone | 0.80 |
| | | | 300 | Tint | 0.59 |
| | | | 1000 | Tint | 1.27 |
| 235-0170 PR 170 | | | 300 | Masstone | 2.12 |
| | | | 1000 | Masstone | 3.27 |
| | | | 300 | Tint | 17.11 |
| | | | 1000 | Tint | 21.70 |
| 235-1170 PR 170 | | | 300 | Masstone | 2.14 |
| | | | 1000 | Masstone | 3.76 |
| | | | 300 | Tint | 4.02 |
| | | | 1000 | Tint | 16.00 |
| Example 2 (Red) | $NO_2$ | $NO_2$ | 300 | Masstone | 1.56 |
| | | | 1000 | Masstone | 2.08 |
| | | | 300 | Tint | 3.61 |
| | | | 1000 | Tint | |

The paint containing the pigment of the present invention has DE values equal to or smaller than paint containing a conventional pigment.

Those skilled in the art having the benefit of the teachings of the present invention as hereinabove set forth, can effect numerous modifications thereto. These modifications are to be construed as being encompassed within the scope of the present invention as set forth in the appended claims.

What is claimed is:

1. A bis-azo/hydzone pigment of the formula (V):

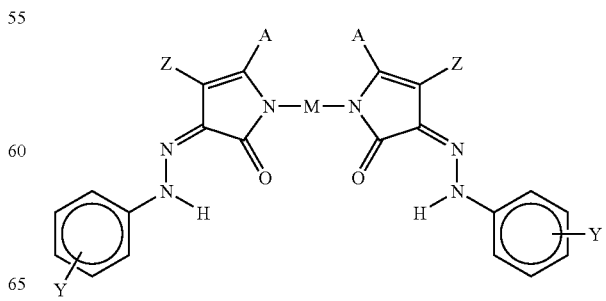

wherein:
- A is a substituted or unsubstituted aryl or substituted or unsubstituted heteroaryl radical;
- Y is hydrogen, alkyl, alkoxy, amine, nitro, carboxylic acid, carboxylic acid ester, or a substituted or unsubstituted fused ring;
- Z is hydrogen, CO—X—B, CN or COCH$_3$;
- B is hydrogen, or a primary aliphatic, carbocyclic, aryl or heterocyclic radical;
- X is a divalent O or NH radical; and
- M is a divalent alkyl, substituted or unsubstituted aryl or substituted or unsubstituted heteroaryl radical, where the substituent may be halogen, alkyl or alkoxy.

2. The bis-azo/hydrazone of claim 1, wherein A is a substituted or unsubstituted aryl radical, Z is CO—X—B, B is a primary aliphatic radical, and X is a divalent oxygen radical.

3. The bis-azo/hydrazone of claim 1, wherein A is a substituted or unsubstituted aryl radical, Z is CO—X—B, B is an aryl radical, and X is divalent NH radical.

4. The bis-azo/hydrazone pigment of claim 1, wherein M is a divalent aryl or alkyl radical.

5. A process for preparing a bis-azo/hydrazone-; pigment of the formula (V)

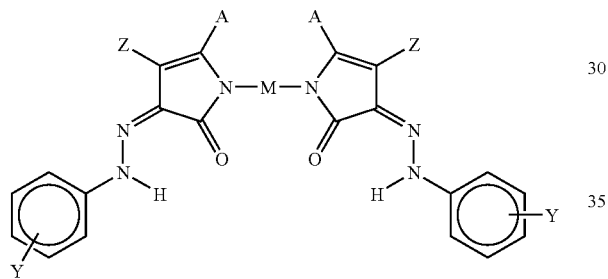

wherein:
- A is a substituted or unsubstituted aryl or substituted or unsubstituted heteroaryl radical;
- Y is hydrogen, alkyl, alkoxy, amine, nitro, carboxylic acid or a substituted or unsubstituted fused ring;
- Z is hydrogen, CO—X—B, CN or COCH$_3$:
- B is hydrogen or a primary aliphatic, carbocyclic or aryl or heterocyclic radical;
- X is a divalent O or NH radical; and
- M is a divalent substituted or unsubstituted aryl radical, a divalent substituted heteroaryl radical, where the substituent may be halogen, alkyl or alkoxy;

comprising reacting a compound of the formula

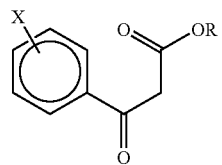

wherein: X is as previously defined and R is a straight or branched chain C$_1$–C$_{18}$ alkyl, C$_7$–C$_{18}$ aralkyl or aryl; with a diamine of the formula H$_2$N—M—NH$_2$ where M is as defined above: to produce a compound of the formula

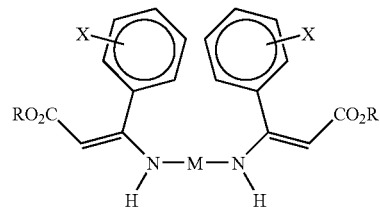

wherein: X, R and M are as defined above;
which is then reacted with oxalyl chloride (COCl)$_2$ to produce a compound of the formula

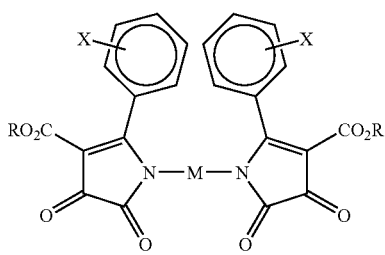

wherein X, R and M are as defined above;
which is then reacted with a compound of the formula

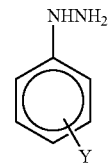

wherein: Y is as defined above.

6. A process for-; preparing a bis-azo hydrazone pigment of the formula (V)

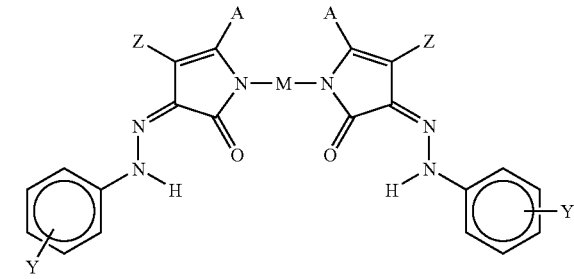

wherein:
- A is a substituted or unsubstituted aryl or substituted or unsubstituted heteroaryl radical;
- Y is hydrogen, alkyl, alkoxy, amine, nitro, carboxylic acid or a substituted or unsubstituted fused ring;
- Z is hydrogen, CO—X—B, CN or COCH$_3$;
- B is hydrogen or a primary aliphatic, carbocyclic or aryl or heterocyclic radical;

X is a divalent O or NH radical; and
M is a divalent substituted or unsubstituted aryl radical, a divalent substituted heteroaryl radical, where the substituent may be halogen, alkyl or alkoxy;
comprising reacting a compound of the formula

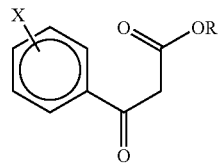

wherein: X is as defined above and R is a straight or branched chain $C_1$–$C_{18}$ alkyl, $C_7$–$C_{18}$ aralkyl or aryl;
with a compound of the formula $ClCH_2CO_2R$
wherein: R is as defined above;
to produce a compound of the formula

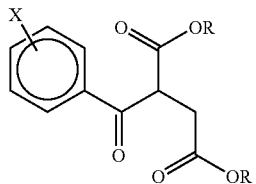

wherein: X and R are as defined above;
which is then reacted with a diamine of the formula $H_2N$—$M$—$NH_2$
wherein: M is as defined above;
to produce a compound of the formula

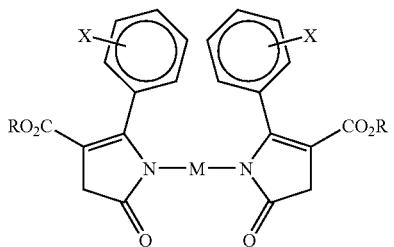

wherein: X, R and M are as defined above;
which is then reacted with a compound of the formula

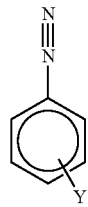

wherein: Y is as defined above.

* * * * *